United States Patent [19]

Gade

[11] Patent Number: 4,945,896

[45] Date of Patent: Aug. 7, 1990

[54] SURGICAL RETRACTOR ASSEMBLY HAVING TISSUE VIABILITY SENSOR EMBEDDED THEREIN

[76] Inventor: George F. Gade, 307 Placentia Ave., Suite 205, Newport Beach, Calif. 92660

[21] Appl. No.: 301,614

[22] Filed: Jan. 24, 1989

[51] Int. Cl.$^5$ ............................................. A61B 17/02
[52] U.S. Cl. ...................................... 128/20; 128/691
[58] Field of Search ................ 128/20, 691, 664, 666

[56] References Cited

U.S. PATENT DOCUMENTS

| | | | |
|---|---|---|---|
| 3,888,117 | 6/1975 | Lewis | 128/20 |
| 4,230,122 | 10/1980 | Lubbers et al. | 128/691 |
| 4,784,150 | 11/1988 | Voorhies | 128/20 |

FOREIGN PATENT DOCUMENTS 165523  12/1985  European Pat. Off. ............ 128/691

Primary Examiner—Edward M. Coven
Assistant Examiner—Mark S. Graham
Attorney, Agent, or Firm—Harness, Dickey & Pierce

[57] ABSTRACT

A surgical retractor is disclosed having a generally flat malleable blade with a miniature metabolic parameter sensor embedded or removably inset into the blade. The sensor detects physiologic and metabolic parameters to monitor tissue viability of the tissue underlying the retractor.

11 Claims, 3 Drawing Sheets

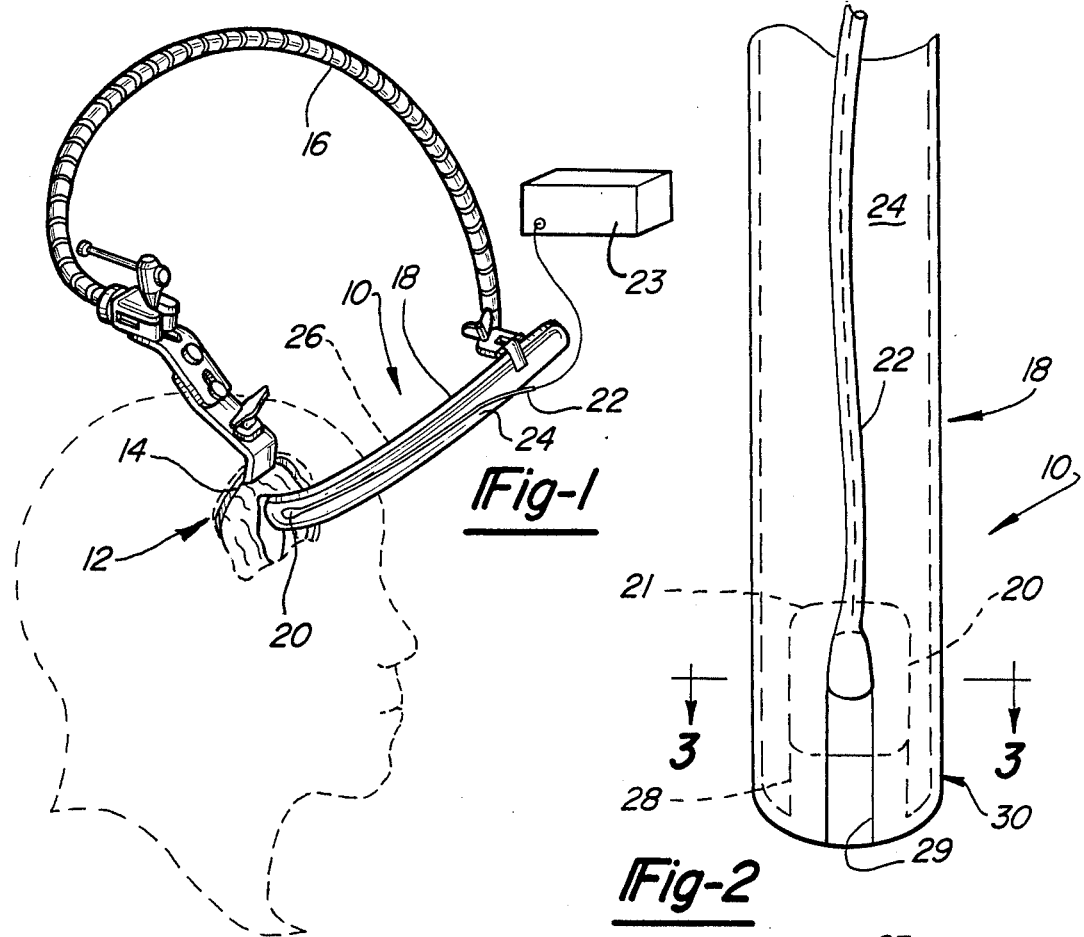
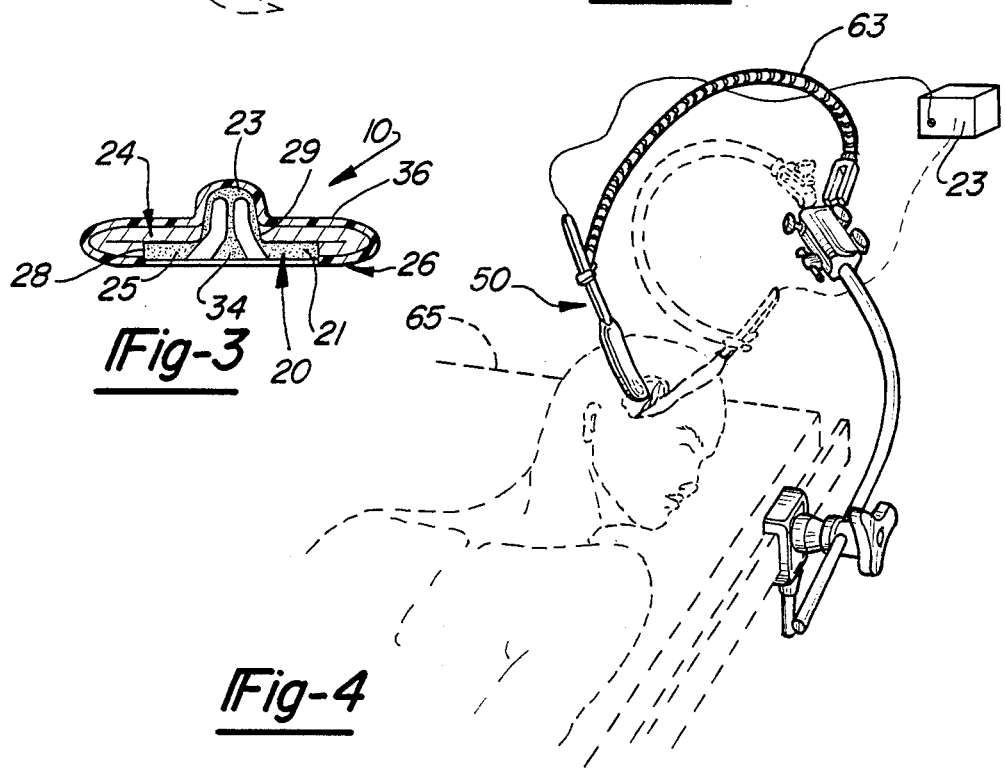

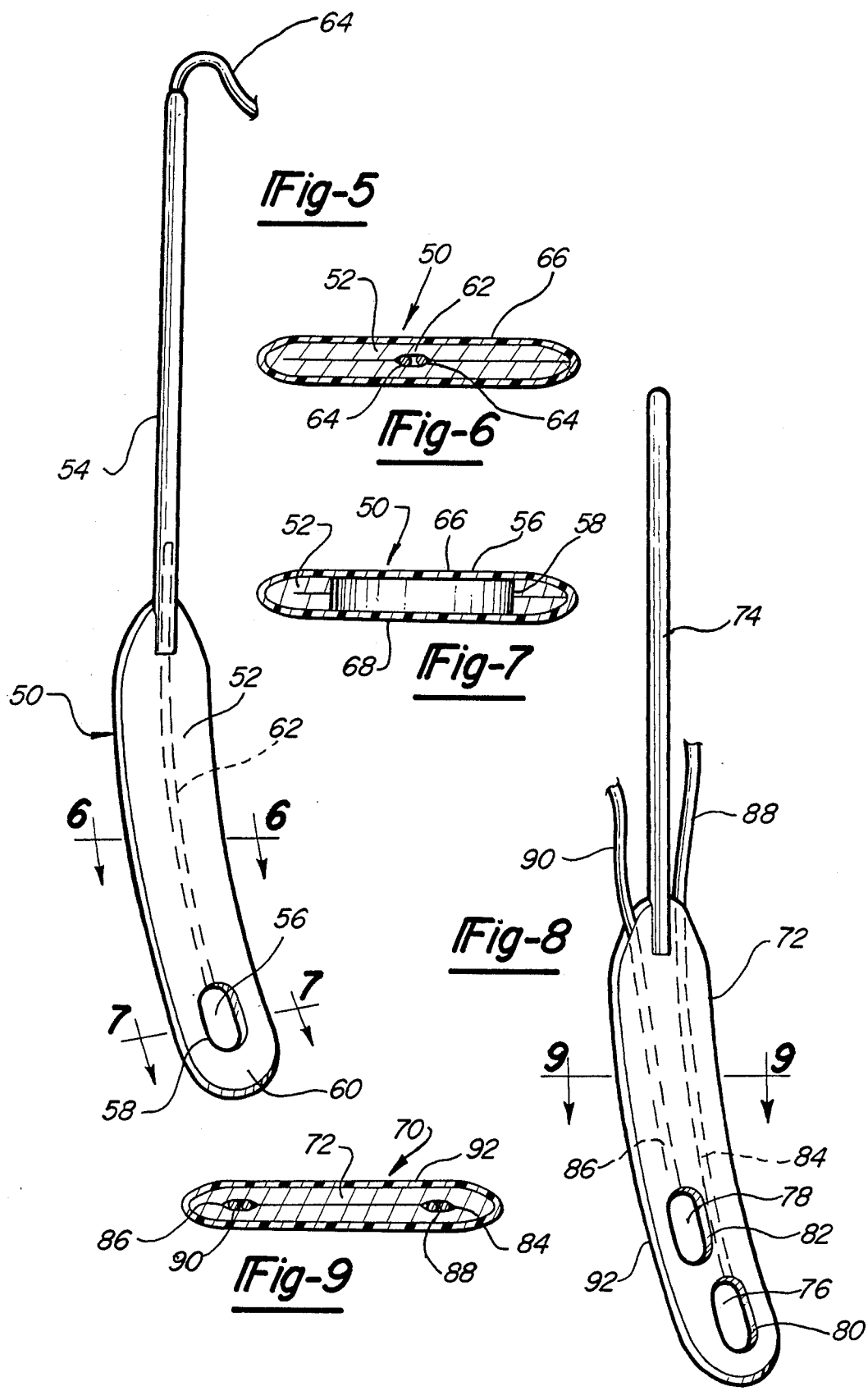

SURGICAL RETRACTOR ASSEMBLY HAVING TISSUE VIABILITY SENSOR EMBEDDED THEREIN

BACKGROUND OF THE INVENTION

This invention relates generally to surgical retractors and more particularly to a surgical retractor assembly having an embedded sensor for detecting metabolic activity and viability of the underlying tissue during surgery and a monitoring system for displaying a signal representative of this activity.

A surgical retractor is used to retract or spread apart overlying tissue and/or organs in order that an internal organ or an underlying organ or particular piece of tissue may be exposed during a surgical procedure. It basically acts as an extra hand. The retractor is in turn usually held in place by a mechanical arm arrangement fixed to the surgical table or to a portion of the patient's body. Surgical retractors typically take the form of a blade having a generally flat shape that is malleable so as to allow the surgeon to bend the blade into a particular shape that may be required in a particular case.

Some types of tissues or organs, such as the brain, are extremely sensitive to externally applied pressure and movement. Brain tissue is the most sensitive of any body tissue to movement and pressure. To protect the brain from damage, the brain is encased in a durable sheath generally known as the dura mater which is in turn enclosed within the skull. In many brain procedures a portion of the skull is removed and an incision made through the dura mater thus exposing the delicate brain tissue. The brain tissue is then carefully separated and retracted in order for the surgeon to view and reach the underlying tissue. A surgical retractor is used to hold the brain tissue in a retracted position so as to expose the underlying portion of the brain during the procedure. The pressure exerted by the retractor often results in impaired blood flow and oxygen starvation of the underlying brain tissue. This, in turn, leads to tissue injury. Accordingly, pressure exerted by the retractor must be minimized and carefully controlled.

Neurosurgeons have historically relied on feel, experience, and judgement to gauge the degree of retraction pressure which is safe and tolerable to the underlying brain tissue. However, the brain tissue in some patients is more sensitive than others and therefore what may be safe for one patient may not be for another. Furthermore, in an individual patient, alterations in blood oxygenation, cerebral blood flow and brain metabolic demands during surgery may make a degree of brain retraction (and hence compression) which was well tolerated at one point during surgery dangerous and harmful at another.

Several methods have been developed to try to measure the pressure being applied by a retractor utilized in these types of operations. One such retractor is disclosed in U.S. Pat. No. 4,263,900. This instrument includes an inflatable envelope between the blade and the tissue having a pair of electrodes positioned therein which intermittently contact each other in response to fluid pressure inside the enclosure. Contact closure increases fluid pressure within the enclosure. When the contacts open, the pressure increase is stopped. Therefore, when a balance is reached, the internal pressure corresponds to the pressure being applied by the retractor to the underlying tissue. Another approach is to place a piezo-resistive strain gauge on the retractor to directly sense and measure the force being applied.

However, pressure measurement is only an indirect gauge of the safety of a particular degree of brain retraction. It is the effect of that pressure on the blood flow, oxygenation and metabolism of the tissue underlying the retractor which is important. Hence, it is these parameters that should be monitored to prevent overretraction and resulting tissue damage.

It is therefore an object of the present invention to provide a surgical retractor having an integral sensor in the blade to detect and monitor the oxygen content of the tissue underlying the retractor blade.

It is another object of the present invention to provide a surgical retractor having a sensor embedded therein to directly monitor micro blood flow in the underlying tissue.

It is another object of the present invention to provide a retractor having a removable sensor in the blade which monitors the intracellular metabolic state of the underlying tissue.

It is another object of the present invention to provide a monitoring system for displaying measured parameters of the activity of the tissue underlying the surgical retractor.

SUMMARY OF THE INVENTION

A surgical retractor assembly is provided according to the teachings of one embodiment of the present invention for retracting and holding soft body tissue such as brain tissue in a stationary retracted position while monitoring the viability of the soft body tissue underlying the retractor. This is preferably accomplished by way of a sensor mounted in a smooth, generally flat, elongated blade. The smooth underside of the blade contacts the soft body tissue when the blade is positioned to retract the tissue. The blade has an aperture in the underside in which the sensor is mounted so as to be positioned directly against the underlying tissue. The sensor has a flat surface and forms a portion of the underside surface contacting the soft body tissue. Also included within the blade may be a hollow bore for passage of electrical lead wires or optical fibers from the sensor to feed a signal to external signal processing equipment.

The sensor embedded in the blade may take the form of any of several sensing devices which directly measures a parameter indicative of cellular metabolism, tissue blood flow, or tissue oxygenation. This allows the surgeon to accurately control and minimize the disturbance of the brain tissue thus minimizing the potential for permanent damage.

A second embodiment of the present invention is similar to the first, above described, except that it includes a removable detector positioned in a slot in the underside surface of the retractor blade. In this embodiment, a sensor may be selected which is tailored to the specific tissue underlying the blade or may be changed according to the requirements of a particular surgical procedure.

A third embodiment of the present invention includes a plurality of sensors strategically mounted in the blade so as to monitor several parameters such as surface oxygen tension, blood flow and tissue metabolism simultaneously.

A monitoring system using the surgical retractor according to the present invention includes one or more sensors embedded or inset in the retractor blade, a signal processing unit and a display unit coupled together by appropriate lead wires or optical bundle leads. The signal processing unit may be a multi-channel processor if multiple sensors are used. The unit converts the signals from the sensors and amplifies the converted waveforms or it may directly amplify the optical or electrical waveform, as appropriate, for the detector type. The amplified electrical signal for each detector is then fed to a display unit which may be a strip chart recorder, CRT display, or converted to an audio tone output.

An audio tone generator may be particularly suited for micro surgical procedures where the physician and his/her assistants have no time to observe a visual indication. The pitch of the audio tone or the duration of tone pulses may be used to indicate the status of the underlying tissue. Alternatively, an alarm threshold may be established to produce a tone or other output only if the sensed variable deviates from a permissible window of values, either high or low. In this way, the audio output would not be an annoying background noise.

Other objects, features and advantages of the present invention will become apparent from a reading of the following detailed description and appended claims when taken in conjunction with the accompanying drawing.

BRIEF DESCRIPTION OF THE DRAWING

FIG. 1 a perspective view of a first embodiment of the retractor according to the present invention mounted on a flexible fixed arm secured to a patient's skull;

FIG. 2 is a fragmentary top view of the distal end of the retractor shown in FIG. 1;

FIG. 3 is a sectional view of the retractor taken along the line 3—3 in FIG. 2;

FIG. 4 is a perspective view of a second embodiment of the retractor according to the present invention mounted on a flexible arm which is attached to the surgical operating table;

FIG. 5 is an enlarged perspective view of the retractor shown in FIG. 4;

FIG. 6 is a sectional view of the retractor blade taken along the line 6—6 in FIG. 5;

FIG. 7 is a partial sectional view of the retractor blade taken along line 7—7 in FIG. 5;

FIG. 8 is a perspective view of an alternative third embodiment of the retractor according to the present invention;

FIG. 9 is a sectional view of the alternative third embodiment taken along the line 9—9 in FIG. 8.

DETAILED DESCRIPTION OF THE PREFERRED EMBODIMENTS

Figure 10:
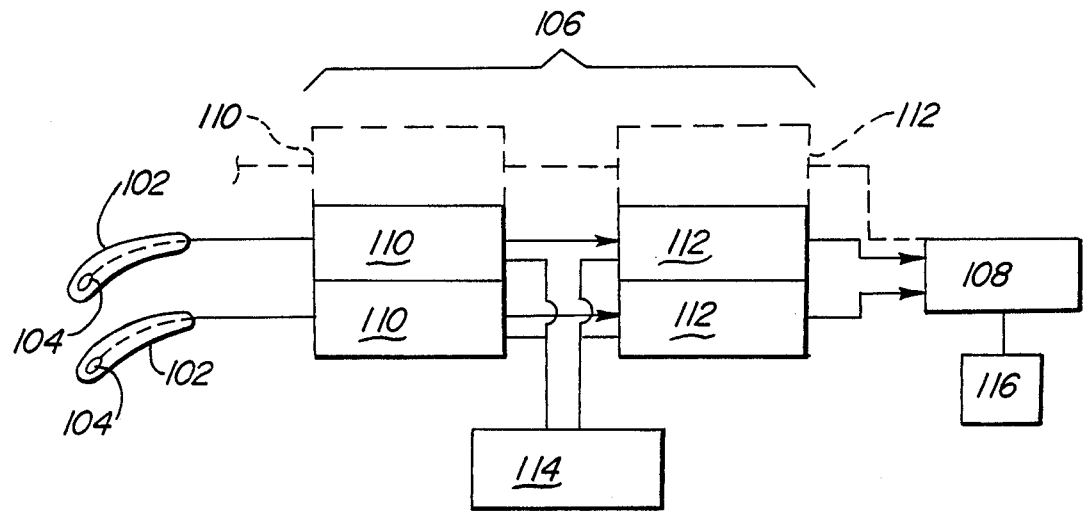
FIG. 10 is a block diagram of a monitoring system according to the present invention.

A surgical retractor 10 according to a first embodiment of the present invention is shown in FIG. 1. The surgical retractor 10 is illustrated inserted within a surgical cavity 12 in a patient's skull 14. The surgical retractor 10 is held in a stationary position in the cavity 12 by a flexible support arm assembly 16 which is clamped in position and fastened to the patient's skull 14.

FIG. 1 is one exemplification of the use of the surgical retractor according to the present invention utilizing a human skull 14 to schematically illustrate the placement of the retractor. As shown, the surgical retractor 10 includes a blade 18, a removable sensor 20 inset in the blade 18 and fiber optic bundles or electrical leads 22 which are carried on the upper side 24 of the blade 18. The leads 22 are connected to suitable external processing and display equipment represented by box 23. Elongated blade 18 may be formed from a flattened tube of malleable metal such as a soft steel alloy or aluminum. The blade should be malleable to allow the surgeon to bend the blade according to the desired placement in cavity 12. Accordingly, leads 22 are flexibly secured to the upper side 24 of the blade 18 to allow for this bending.

The sensor 20 is positioned flush with the surface of the underside portion 26 of the blade 18 in a slot 28 formed in the underside portion 26 at the distal end 30. The distal end 30 is positioned in surgical cavity 12 so that the underside portion 26 and the sensor 20 are directly against the underlying soft brain tissue 32 to hold the soft brain tissue 32 in a retracted position while the required surgical procedure is performed. The sensor 20 is of generally flat shape so as to maintain the generally flat, smooth underside surface of blade 18.

Depending on the sensor design, a transparent membrane 34 may be positioned between the sensor 20 and the soft body tissue. The entire blade 18 except for the sensor inset in slots 28 is provided with a coating or cover 36. Cover 36 is made of a polymeric material such as Teflon which does not adhere to the brain tissue 32. This coating or cover may be permanent or removable depending on the particular blade design. In the embodiment shown in FIGS. 1 through 3, the optical fiber bundles or leads 22 extend through a slot 29 through the upper side 24. This allows for replacement of the sensor 20 with a different type of sensor.

The slot 29 is in the upper side 24 of blade 18 is narrower and superimposed over the slot 28 in the underside 26 at the distal end 30. Each of the slots 28 and 29 have an open end so as to receive the sensor 20. Sensor 20 has a flat plate portion 21 which rests generally flush with the surface of underside 26 and a raised portion 23 to accommodate and pass leads 22 from the plate portion 21. The slot 29 receives and guides the raised portion 23 with leads 22 from the sensor and coacts with the flat portion 21 and portion 23 to retain the sensor 20 in proper position when the sensor 20 is fully inset in distal end 30.

The flat plate portion 21 of sensor 20 is preferably an elongated generally rectangular plate body with rounded corners to facilitate insertion of the sensor 20 in the slot 28 in blade 18. The flat plate shape also ensures a fixed orientation of the sensor face 25 in the distal end 30 with respect to the surface of the underside 26 of blade 18. The face 25 may be slightly offset from the underside 26 or may be flush as appropriate for the particularly sensor type and cover design so that when completely assembled, the underside 26 of blade 18 with sensor 20 and cover 36 installed presents a smooth surface to contact the underlying brain tissue.

One example of such a suitable sensor is a Clark polarographic electrode which provides a real time assessment of organ perfusion and oxygen transport. The Clark electrode directly senses the surface oxygen tension (pO$_2$) in the underlying brain tissue and produces an electrical signal proportionally. As the pO$_2$ content is directly related to the blood flow and metabolism within the brain cells, the pO$_2$ is a direct measure of the tissue viability underlying the retractor blade.

Another form of sensor that can be used in the present invention detects micro circulation of red blood cells. This sensor employs a double wave length laser Doppler velocimeter system to directly monitor micro circulation of blood within the tissue underlying the retractor blade. In the velocimeter (which is illustrated in FIGS. 1–3), a laser light beam is directed to the tissue surface by an optical fiber bundle lead 22 passing along the blade 18 and onto the tissue 32 through a fiber optic sensor 20 mounted in the slot 28 in the blade 18. The beam is scattered by the moving red blood cells as well as the fixed structures of the underlying tissue. Another optical fiber bundle 22 or the same fiber bundle 22 collects the back scattered light, a small fraction of which is frequency shifted by the flowing red blood cells according to the Doppler effect. The detection of these shifts is founded on the heterodyning principal. The frequency spectrum of heterodyned beats represents the Doppler spectrum which, in this case, is a function of the red cell velocity. Thus this sensor directly measures the red blood cell flow in the micro circulatory network of the underlying tissue. Such a device is described in more detail in "A Double Wave Length Doppler System to Investigate Skin Micro Circulation", Luke Dutiel et al, I.E.E.E. Transactions on Biomedical Engineering, Jun. 1985.

A third sensor type which may be used in the present invention involves fiber optic surface fluorometry and reflectometry. In this case, the optical sensor in the retractor blade is a fiber optic window and light guide. The fiber optic bundle light or guide extends from the sensor along the retractor blade and out to a remote photomultiplier tube where any transmitted light is amplified and converted into an appropriate electronic signal. During the electron transport process which occurs in cellular respiration, some compounds autofluoresce at certain frequencies. Other compounds may fluoresce upon external light stimulation at a different frequency. In the tissue underlying the retractor blade, the autofluorescence and stimulated fluorescence of active compounds in the mitachondria of the brain cells can be directly detected.

The autofluorescence and stimulated fluroescence of mitachondrial Nicotinamide Adenine Dinucleotide Hydride (NADH) molecule is directly related to the metabolic state of the mitochondria and hence the viability of entire underlying tissue. In this method of detection, autofluorescence may be directly detected or the exposed brain adjacent the sensor can be illuminated by light passing through the light fibers to excite the NADH within the mitochondria and the emitted fluorescence light from the mitochondria is measured. The activity of the NADH molecule is a sensitive component of the respiratory chain within the cell and therefore is a direct measurement of metabolism and intracellular viability.

A second embodiment of the surgical retractor according to the present invention is illustrated in FIGS. 4 through 7. Surgical retractor 50 includes a generally flat malleable metal blade 52 which is brazed, welded, or otherwise fastened to a hollow tubular handle 54. A miniature flat sensor 56 of one of the types described above is embedded in an aperture 58 adjacent distal end 60 of the blade 52.

The blade 52 may be formed from a flat sheet of malleable metal that is folded in half lengthwise as shown in the cross sectional views of FIGS. 6 and 7. The sandwiched metal of the blade 52 forms a longitudinal bore 62 which passes through the length of the blade 52. The bore 62 connects and communicates between the hollow handle 54 and the aperture 58. The bore 62 and the hollow handle 54 provides a passage for the optic fiber bundles or lead wires 64 from the sensor 56 to connect the sensor 56 to remote signal processing equipment (not shown). The blade 52 is then coated with a polymeric material 66 such as Teflon or other similar material that will not adhere to the soft brain tissue.

An alternative arrangement for securing the surgical retractor of the present invention in place is illustrated in FIG. 4 wherein the surgical retractor 50 is mounted to a flexible arm 63 which is in turn secured to the side of the operating table 65. Additional retractors may be mounted in similar fashion as suggested by the dotted lines shown in FIG. 4.

The sensor 56 embedded in the blade 52 may be one of a variety of designs as discussed above with reference to the first embodiment. For example, the sensor 56 may be a Clark electrode for monitoring the surface oxygen tension of the underlying tissue. In this case, an oxygen permeable membrane 68 would be positioned between the face of the sensor 56 and the tissue underlying the retractor blade 52. Alternatively, an optical fiber sensor could be utilized with or without an optically transparent membrane over the sensor face to transmit a light signal utilized in the laser Doppler velocimeter or in the NADH fluorescence spectrometry methods also described above.

A third embodiment of the present invention is illustrated in FIGS. 8 and 9. In this embodiment, the surgical retractor 70 includes a malleable flat blade 72, handle 74, and a pair of sensors 76 and 78 mounted in a pair of apertures 80 and 82 respectively. A pair of bores 84 and 86 provide passage for the lead wires 88 and 90 longitudinally through the blade 72.

In this embodiment, the surgical retractor 70 can have embedded therein a Clark electrode for monitoring oxygen content directly in the underlying tissue and a different electrode, for example, an NADH fluorescence device in the other aperture. In this case, the leads 88 would be electrical wires and the leads 90 would be glass fiber bundles passing providing the required signals to and from the sensors.

As in the previous embodiments, the blade 72 is provided with a coating or cover 92 of Teflon or other polymeric material to prevent adherence of the metal to the soft brain tissue. The coating or cover 92 is absent from the face of the sensors 76 and 78 against the underlying tissue. In place of the coating 92 over the exposed surface of the sensors 76 and 78 is either an optically transparent film over the double wave length laser Doppler velocimeter or the NADH fluorometer for measuring blood flow and cell metabolism respectively or an oxygen permeable membrane if a Clark oxygen sensor is embedded within one of the apertures 80 or 82 in the blade 72.

In all of the above embodiments, the cover or coating of polymeric material must permit thermal or chemical sterilization of the retractor. Use of a high temperature polymeric coating such as Kevlar, a trademark of duPont, may be preferred because chemical sterilization methods with ethylene oxide will attack most polymers. Therefore, dry heat or steam may be used, hence the requirement for a high temperature polymer coating. Kevlar is an aromatic polyamide polymer having a melting temperature higher than that required for sterilization. It is also non-reactive to soft body tissue.

A monitoring system which utilizes one or more of the retractors according to the present invention is illustrated in a block diagram form in FIG. 10. A monitoring system 100 according to the present invention includes one or more retractors 102, each having at least one sensor 104 embedded therein to monitor the viability of the underlying soft body tissue, a signal processing unit 106, and a display device 108.

The signal processing unit 106 is a multi-channel unit designed to accommodate the maximum anticipated number of sensors that may be utilized. In addition, each of these channels may be designed to accommodate an optical sensor input as in the laser Doppler velocimeter or the NADH fluorometer described above. In the case of a Clark oxygen sensor, an electronic channel would be utilized. Each of the channels in the signal processing unit 106 comprises a signal conversion portion 110 and an amplifying portion 112. Each portion is fed by a processing unit power supply 114. The signal conversion portion 110 converts the input signal from the sensor to an appropriate electronic waveform which can be amplified and subsequently displayed. The amplifier portion 112 amplifies the output of the signal conversion portion 110 to produce an output voltage or current signal appropriate to the display device 108. The signal processing unit power supply 114 provides appropriate electrical power and may also provide the necessary source of collimated light required with the laser Doppler velocimeters or fluorometer sensors.

The display device 108 may be cathode ray tube (CRT), a strip chart recorder, an audio speaker, or any of a number of conventional alarm modules and indicating devices. Preferably, a strip chart recorder may be used for a permanent record and an audio display 116 for audible monitoring.

The audio display device 116 is particularly well suited for use during a surgical procedure where visual monitoring is limited. For example, during micro surgery, the surgeon may not be able to look at a visual monitor but can listen for abnormal tones produced by an audio speaker. Alternatively, the signal processor unit 106 may include capability to establish a threshold window below which no tone is produce and above which a tone would indicate that the cellular activity beneath the retractor blade is outside of an acceptable band. The audio output device 116 is particularly well suited to keep the surgical team apprised of tissue condition and continuously warn the team of tissue conditions which would lead to tissue death and the ensuing complications.

While this invention has been described in connection with several particular examples, various other alternative physical configurations of the surgical retractor blade are envisioned by the present invention. The two blade configurations illustrated in the drawing are merely illustrative and not intended to limit the scope of the present invention. In addition, other types of detectors or sensors can be embedded within the surgical retractor blade so as to be positioned against the underlying soft tissue. The three sensors discussed are merely representative of possible sensor types which can be used provided sufficient miniaturization permits their use. Still other modifications will become apparent to those skilled in the art after having the benefit of study of the specification, drawing, and following claims.

What is claimed is:

1. A retractor assembly for retracting and holding soft body tissue in a stationary retracted position and monitoring the viability of said soft body tissue underlying said retractor, said assembly comprising:
   a generally flat, elongated blade insertable within a surgical cavity, said blade having an underside, an upper side, a distal end portion and a proximal end portion, said underside of said distal end portion contacting said soft body tissue when said blade is positioned in said cavity to retract said tissue, said blade having a first slot through its upper side and a second slot through its under side;
   sensor means embedded in said distal end portion of said blade for detecting physiologic and metabolic status of said underlying tissue and for producing a signal representative of said status, said sensor means removably inset in said second slot; and
   conduit means for passing said signal from said sensor means along said blade and from said distal end to said proximal end whereby the signal can be connected to a signal processor for remotely processing and displaying the detected status in the underlying tissue, said conduit means being mounted to the upper side of said blade and passing through said first and second slots to said sensor means.

2. The retractor assembly according to claim 1 wherein said sensor means is an oxygen tension sensor responsive to the surface oxygen concentration in said tissue.

3. The retractor assembly according to claim 1 wherein said blade is coated with a polymeric material to prevent adherence of said blade to said soft tissue.

4. The retractor assembly according to claim 1 wherein said sensor means is a fiber optic window for conducting light through a fiber optic bundle lead in said conduit means to and from said underlying soft body tissue.

5. The retractor assembly according to claim 1 wherein said blade is formed of a piece of flat sheet metal folded lengthwise.

6. The retractor assembly according to claim 1 wherein said blade is formed of a flattened tube of malleable metal.

7. The retractor assembly according to claim 1 wherein said sensor means is covered with a transparent membrane to protect said sensor and allow light passage through said membrane.

8. The retractor according to claim 2 wherein said blade includes a cover of a polymeric material and an oxygen permeable membrane covers said oxygen sensor.

9. The retractor according to claim 1 wherein each of said slots has an open end and a closed end, said slots being aligned and superimposed so that said sensor means is installed through said open ends, said slots slidably receiving and holding a portion of said sensor means substantially flush with the underside of said blade.

10. The retractor assembly of claim 1 including a tissue viability monitoring system comprising:
    a signal processing means connected to the sensor means by the conduit means for converting the signal from the sensor means to an electrical signal and amplifying said signal; and
    display means coupled to said signal processing means for displaying said signal.

11. The system according to claim 10 wherein said display means comprises a multi-channel strip chart recorder and an audible speaker, said speaker producing an audio tone having a pitch representative of said activity in said underlying body tissue.

* * * * *